(12) United States Patent
Hoctor et al.

(10) Patent No.: US 8,315,224 B2
(45) Date of Patent: Nov. 20, 2012

(54) METHODS AND SYSTEMS FOR REUSE OF RADIO RESOURCES IN MEDICAL TELEMETRY NETWORKS

(75) Inventors: Ralph Thomas Hoctor, Saratoga Springs, NY (US); David Michael Davenport, Niskayuna, NY (US); Neal John Seidl, Pewaukee, WI (US); Matthew George Grubis, New Berlin, WI (US); Sahika Genc, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 271 days.

(21) Appl. No.: 12/691,962

(22) Filed: Jan. 22, 2010

(65) Prior Publication Data

US 2011/0183698 A1    Jul. 28, 2011

(51) Int. Cl.
  *H04W 4/00*   (2009.01)
  *H04B 7/212*   (2006.01)
  *H04J 3/00*   (2006.01)
  *H04J 4/00*   (2006.01)
(52) U.S. Cl. ........ 370/330; 370/341; 370/344; 370/345; 370/436
(58) Field of Classification Search .......... 370/328–330, 370/341, 343–345, 436
See application file for complete search history.

(56) References Cited

U.S. PATENT DOCUMENTS

| 7,133,380 | B1 * | 11/2006 | Winters et al. ................ 370/329 |
| 2002/0183069 | A1 * | 12/2002 | Myr .............................. 455/456 |
| 2004/0214582 | A1 * | 10/2004 | Lan et al. ................... 455/452.2 |
| 2006/0209803 | A1 * | 9/2006 | Rajaniemi et al. ............ 370/352 |
| 2011/0136493 | A1 * | 6/2011 | Dimpflmaier et al. ........ 455/450 |

OTHER PUBLICATIONS

"IntelliVue MP2 Patient Monitor," Royal Philips Electronics, Philips M8102A Technical Data Sheet, 2007, pp. 1-26.
"ApexPro CH," Enterprise-wide telemetry, GE Healthcare, 2008, pp. 1-8.
"ApexPro FH Telemetry Transceiver," Scalable frequency-hopping technology, GE Healthcare, 2009, pp. 1-4.

* cited by examiner

*Primary Examiner* — Ronald Abelson
(74) *Attorney, Agent, or Firm* — Scott J. Asmus

(57) ABSTRACT

Methods and systems and computer program products for reusing radio resources in a medical telemetry networks are provided. The method receives at a server, traffic information for a plurality of mobile transceivers, from a plurality of distributed receivers. The method identifies time slot assignments and frequency channel assignments of the plurality of mobile transceivers based on traffic information. The method then updates one or more time slot assignments and/or one or more frequency channel assignments based, at least in part, on traffic information. Finally, the method broadcasts updated instances of the time slot assignments and updated instances of frequency channel assignments.

24 Claims, 11 Drawing Sheets

|   | A | B | C | D | E | F | G | H | I |
|---|---|---|---|---|---|---|---|---|---|
| A | 2 | 2 | 2 | 1 | 1 | 1 | 0 | 0 | 1 |
| B | 2 | 2 | 1 | 2 | 1 | 2 | 1 | 1 | 1 |
| C | 2 | 1 | 2 | 2 | 1 | 1 | 0 | 0 | 1 |
| D | 1 | 2 | 2 | 2 | 1 | 2 | 1 | 1 | 1 |
| E | 1 | 1 | 1 | 1 | 2 | 2 | 2 | 1 | 2 |
| F | 1 | 2 | 1 | 2 | 2 | 2 | 1 | 1 | 2 |
| G | 0 | 1 | 0 | 1 | 2 | 1 | 2 | 2 | 1 |
| H | 0 | 1 | 0 | 1 | 1 | 1 | 2 | 2 | 2 |
| I | 1 | 1 | 1 | 1 | 2 | 2 | 1 | 2 | 2 |

502 ⤵

| 160-BIT PREAMBLE | 108-BIT INFO PACKET | CRC | 108-BIT CTRL PACKET | CRC | • • • | 108-BIT CTRL PACKET | CRC | 108-BIT CTRL PACKET | CRC |

STRUCTURE OF DOWNLINK BURST

| 160-BIT PREAMBLE | 108-BIT INFO PACKET | CRC | 108-BIT INFO / DATAPACKET | CRC | • • • | 108-BIT DATA PACKET | CRC | 108-BIT DATA PACKET | CRC |

STRUCTURE OF UPLINK BURST

| | F1 | F2 | F3 | F4 | F5 |
|---|---|---|---|---|---|
| T1 | G | A | F | E | D |
| T2 | G | - | F | E | D |
| T3 | G | - | F | - | D |
| T4 | G | - | F | - | D |
| T5 | G | - | C | - | D |
| T6 | G | - | C | E | C |
| T7 | G | - | C | E | C |
| T8 | G | I | C | E | C |

| | F4 | F5 | F1 | F2 | F3 |
|---|---|---|---|---|---|
| T1 | E | D | G | A | F |
| T2 | E | D | G | - | F |
| T3 | - | D | G | - | F |
| T4 | - | D | G | - | F |
| T5 | - | D | G | - | C |
| T6 | E | C | G | - | C |
| T7 | E | C | G | - | C |
| T8 | E | C | G | I | C |

*FIG. 12B*

METHODS AND SYSTEMS FOR REUSE OF RADIO RESOURCES IN MEDICAL TELEMETRY NETWORKS

BACKGROUND

The invention relates generally to wireless telemetry systems and more particularly to medical telemetry systems for monitoring patients in a hospital.

Patients in a hospital are monitored to obtain physiological data, such as body temperature, pulse rate, heart rate, blood pressure, oxygen saturation, respiratory rate, electrocardiography (ECG or EKG), electromyography (EMG), and electroencephalography (EEG). Wireless medical telemetry systems may be used to perform such monitoring. In wireless medical telemetry systems, a remote telemeter attached to the patient sends the patient's vital physiological data to a monitoring station over a wireless telemetry link. This allows the patient to move around in the hospital as the patient is not tethered to a wire-line telemetry system.

Large hospitals typically need to monitor a large number of patients simultaneously. Generally, large hospitals employ distributed antenna architecture for monitoring the large number of patients. However, this implementation suffers from high noise floors resulting from combining the large number of antenna outputs.

Another method employed by hospitals is cellular medical telemetry network. Cellular medical telemetry networks enhance the monitoring capacity of the medical telemetry system using techniques such as frequency reuse in Frequency Division Multiple Access (FDMA) networks. In FDMA networks, frequency reuse entails the allocation of the same time/frequency resources to mobile transmitters within more than one coverage area. Thus, the maximum number of telemeters in each cell is limited by the frequency channels allocated to the cell. Borrowing frequency channels from neighboring cells partly addresses this shortcoming, although at the expense of depleting the frequency channel capacity of neighboring cells. The movement of a large number of patients into a cell neighborhood, at the same time, may result in service interruption for some patient telemeters. Service interruption in the cellular medical telemetry network is a critical problem and may result in life-threatening events going unreported.

Also, different monitoring systems generate different amounts of data and may require different data transmission rates. Therefore, integration of different monitoring systems may necessitate separate infrastructure for different data transmission rates which may add to the complexity of the wireless medical telemetry system, and/or further compound the problem of limited frequency channels.

As a result, there is a need in the art for methods and systems for overcoming the aforementioned drawbacks associated with present wireless medical telemetry systems.

BRIEF DESCRIPTION

The above and other drawbacks/deficiencies of the prior art may be overcome or alleviated by an embodiment of a method for reusing radio resources in a medical telemetry network. The method receives, at a server, traffic information for a plurality of mobile transceivers, from a plurality of distributed receivers. The method identifies time slot assignments and frequency channel assignments of the plurality of mobile transceivers based on traffic information. The method then updates one or more time slot assignments and/or one or more frequency channel assignments based, at least in part, on traffic information. Finally, the method broadcasts updated instances of the time slot assignments and updated instances of frequency channel assignments.

DRAWINGS

These and other features, aspects, and advantages of the present invention will become better understood when the following detailed description is read with reference to the accompanying drawings in which like characters represent like parts throughout the drawings, wherein:

FIG. 5 illustrates an exemplary packet structures of a broadcast downlink burst, according to one embodiment;

FIG. 6 illustrates an exemplary packet structures of an uplink transmission burst, according to one embodiment;

FIGS. 12A and 12B illustrate exemplary slot maps, according to one embodiment.

DETAILED DESCRIPTION

Patients in a hospital may be monitored in order to obtain vital physiological data, such as, but not limited to, body temperature, heart rate, blood pressure, oxygen saturation and respiratory rate. One well known technique of such monitoring is wireless medical telemetry using the Wireless Medical Telemetry Service (WMTS) spectrum. Disclosed herein is a method for re-using the radio resources in the wireless medical telemetry system in order to monitor a large number of patients simultaneously. The wireless medical telemetry system disclosed herein employs two-way mobile telemeters employing Time Division Multiple Access (TDMA) and Frequency Division Multiple Access (FDMA). Radio-resources, i.e. time slots and frequency channels may be assigned to the mobile telemeters by a central network controller, based on the current traffic conditions of the network. Various embodiments of the invention disclosed herein, may operate in the Wireless Medical Telemetry Service (WMTS) spectrum. The uplink may be located in the 1395-1400 MHz portion of the WMTS spectrum, and the downlink may occupy 2.5 MHz in the 1427-1432 MHz portion of the WMTS spectrum. Generally, WMTS operations are accorded primary status over non-medical telemetry operations in the 1427-1429.5 MHz band, but are treated as secondary to non-medical telemetry operations in the 1429.5-1432 MHz band. However, there are some geographical areas in which WMTS has primary status in the 1429-1431.5 MHz band, but is secondary to non-medical telemetry operations in the 1427-1429 MHz band. Therefore, in various embodiments, the 2.5 MHz downlink band is chosen such that the WMTS has primary status in that band. In various embodiments of the present invention, other portions of the radio spectrum may be used, where efficient spatial re-use of radio resources is required.

Figure 1:
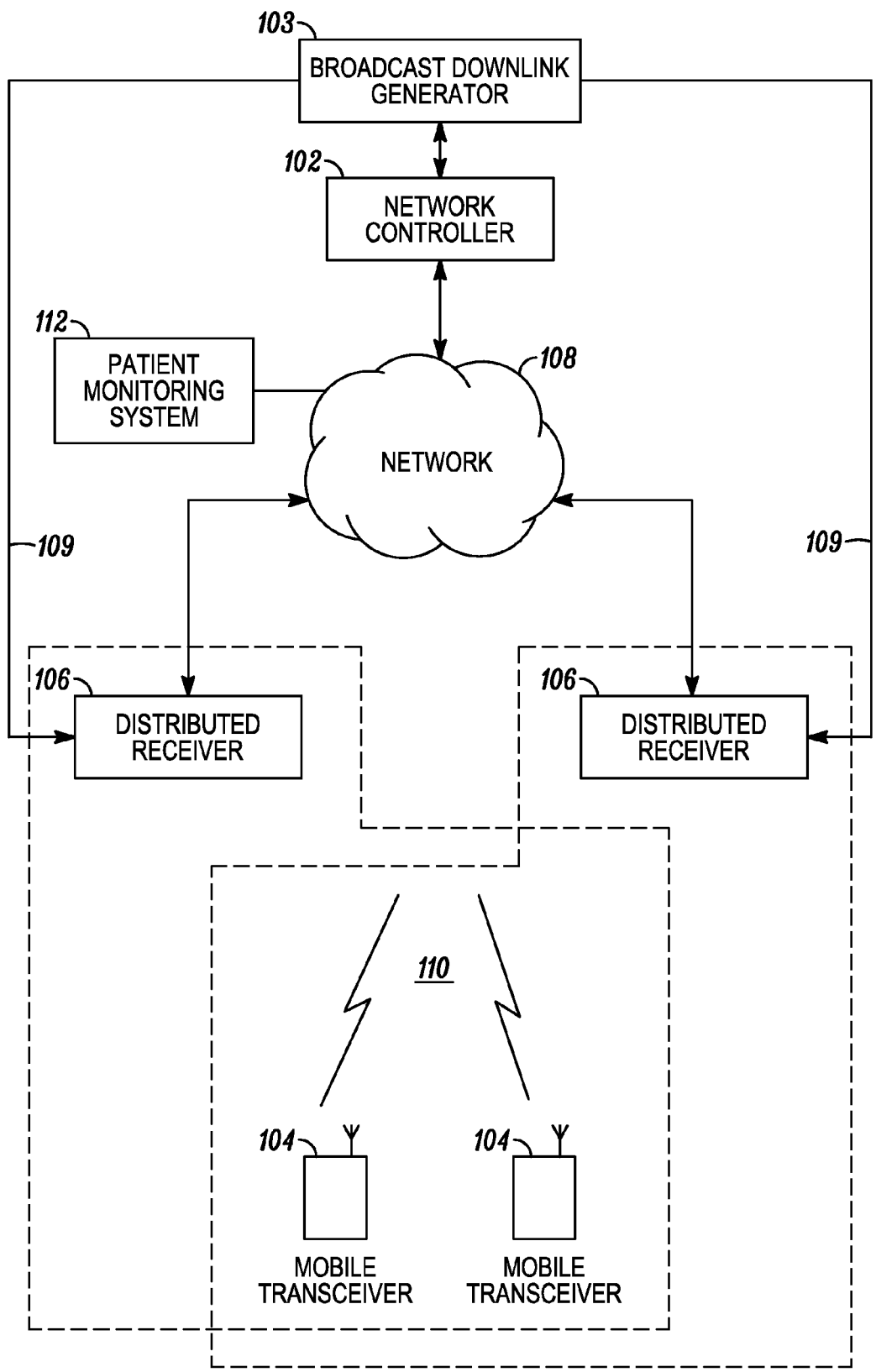
FIG. 1 is an exemplary environment in which a network controller will function, according to one embodiment.

Referring now to the Figures, where the like numbers represent like elements throughout the several views, FIG. 1 is an exemplary telemetry system 100 in which a network controller 102 may operate, according to one embodiment of the present invention. The telemetry system 100 includes the network controller 102, a broadcast downlink generator 103, a plurality of mobile transceivers 104, a plurality of distributed receivers 106, a network 108, a broadcast link 109, a plurality of coverage zones 110, and a patient monitoring system 112. The network controller 102 dynamically assigns time slots and frequency channels to the mobile transceivers 104 based on the traffic conditions, performs requirement-based uplink bandwidth allocation for the mobile transceivers 104, controls transmission power of the mobile transceivers 104, selectively enables forward error correction on the mobile transceivers 104, periodically reassigns time slots and frequency channels for improved uplink bandwidth utilization, and broadcasts alerts and notifications to the mobile transceivers 104.

The network controller 102 receives traffic information for the mobile transceivers 104 through uplink communication from the mobile transceivers 104 and/or the distributed receivers 106. Traffic information includes, without limitation, the number of mobile transceivers 104 in communication with each of the distributed receivers 106, mobile transceiver identifiers of the mobile transceivers 104, presence of the mobile transceivers 104—as to which distributed receiver 106 has best reception of uplink transmissions of the various mobile transceivers 104, and buffer state of the mobile transceivers 104. Traffic information associated with the mobile transceivers 104, such as the mobile transceiver identifier of the mobile transceiver and buffer state of the mobile transceiver 104, may be transmitted by the mobile transceiver 104. Traffic information associated with the distributed receivers 106, such as the number of mobile transceivers 104 in communication with each of the distributed receivers 106 and presence of the mobile transceivers 104 in the coverage zones 110 of each of the distributed receivers 106, may be transmitted by the distributed receivers 106. The process of determining the presence of the mobile transceivers 104 in the coverage zones 110 by the distributed receivers 106 is described in conjunction with FIG. 2. In various embodiments, the mobile transceivers 104 and/or the distributed receivers 106 periodically send uplink frames to the network controller 102 to provide such traffic information. In an embodiment, a mobile transceiver 104 sends and uplink frame to a distributed receiver 106, and the distributed receiver 106 inserts additional traffic information into the uplink frame before sending it to the network controller 102.

The network controller 102 identifies time slot assignments and frequency channel assignments of the mobile transceivers 104, based on the received traffic information. In one embodiment, the network controller 102 receives the mobile transceiver identifier of the mobile transceiver 104, and the time slot and frequency channel associated with the mobile transceiver identifier, from the distributed receivers 106.

The network controller 102 detects the movement of the mobile transceiver 104 from one coverage zone 110 to another. The network controller 102 recognizes the movement of the mobile transceiver 104 using the distributed receiver identifier, and the mobile transceiver identifier. The network controller 102 may compare the current distributed receiver identifier, and the previous distributed receiver identifier associated with the mobile transceiver identifier, to detect the movement of the mobile transceiver 104. The network controller 102 may update the time slot and frequency channel assignments of the mobile transceivers 104 identified to have moved into a different coverage zone 110.

The network controller 102 may consider channel separation constraints for the mobile transceivers 104, for updating the time slot and frequency channel assignments. The channel separation constraints specify the minimum separation of frequency channels required between multiple mobile transceivers 104 transmitting during the same time slots, to prevent RF interference. As the mobile transceiver 104 moves from one coverage zone 110 to another, the time slot and frequency channel assigned to the mobile transceiver 104 for transmitting in the original coverage zone 110 may violate the channel separation constraints in the new coverage zone 110. Therefore, the network controller 102 updates the time slot and frequency channel assignments of the mobile transceiver 104 based on the channel separation constraints. The channel separation constraints may be expressed in terms of a constraint map with respect to the physical layout of the different coverage zones 110 and distributed receivers 106. Exemplary constraint maps are described in conjunction with FIGS. 4A and 4B.

In an exemplary embodiment, the network controller 102 may update the time slot and frequency channel assignments for mobile transceivers 104 considering the presence of the mobile transceiver 104 in the coverage zones 110 of distributed receiver 106, and anticipating the movement of the mobile transceivers 104 into an adjacent coverage zone 110. The network controller 102 may have knowledge of the distributed receiver 106 locations in the hospital facility, and may have logic or algorithms to anticipate the movement of the mobile transceivers 104 from one coverage zone 110 to another, given knowledge of the floor plan topology. For example, patients (and their mobile transceiver 104) being moved from the emergency room (ER) to the intensive care unit (ICU) may only move from the control of the distributed receiver 106 of the ER, to the distributed receiver 106 of the hallway connecting the ER and the ICU, and finally into the control of the distributed receiver 106 of the ICU. The network controller 102 may use the presence of the mobile transceiver 104 in the coverage zones 110 of the distributed receiver 106, during each uplink frame to anticipate movement into a different coverage zone 110. Responsive to such anticipation, the network controller 102 may update the time slot and frequency channel assignments of the mobile transceiver 104.

The network controller 102 then transfers the updated instances of the time slot and frequency channel assignments to the broadcast downlink generator 103. The broadcast downlink generator 103 then broadcasts the updated instances of the time slot and frequency channel assignments, in a downlink frame, to the distributed receiver 106, through link 109. The broadcast downlink generator 103 transmits only the updated instances of the time slot and frequency channel assignments, to conserve the broadcast downlink bandwidth. The broadcast downlink generator 103 may modulate the received time slot and frequency channel assignments to a form suitable for transmission, and then broadcast the received time slot and frequency channel assignments over link 109. Link 109 may be any suitable RF transmission medium such as, but not limited to, a fiber optic cable, a broadband co-axial cable, and the like. After broadcasting an updated time slot and frequency channel assignment of a particular mobile transceiver 104, the network controller 102 listens for uplink transmissions of that mobile transceiver 104 on both, the updated time slot in the updated frequency channel and the original time slot in the original frequency channel of the mobile transceiver 104. The network controller 102 may identify the original time slot in the original frequency channel, as available for next updates, only if the network controller 102 receives traffic information associated with that mobile transceiver 104 on the updated time slot in the updated frequency channel.

In an exemplary embodiment, the network controller 102 may also update the time slot and frequency channel assignments for mobile transceivers 104 that have a different uplink bandwidth requirement. The network controller 102 may receive the uplink bandwidth requirement from the mobile transceivers 104 in the uplink transmissions. The mobile transceiver 104 may transmit the buffer state i.e. the current remaining buffer capacity in every uplink burst 602. The network controller 102 may use the buffer state of the mobile transceiver 104 to update its time slot assignment. If the buffer state indicates that current remaining buffer capacity of the mobile transceiver 104 is lower than a predefined capacity, the network controller 102 assigns additional time slots to the mobile transceiver 104. If the buffer is emptied before all the assigned time slots are used, the network controller 102 may reduce the number of time slots assigned to the mobile transceiver 104.

The telemetry system 100 may also accommodate a variety of patient monitoring applications such as, but not limited to, electrocardiography (ECG or EKG), electromyography (EMG), electroencephalography (EEG), monitoring of vital signs such as body temperature, pulse rate, blood pressure, respiratory rate and the like. Different patient monitoring applications may generate different amounts of diagnostic data, and therefore require transmission at different data rates. The network controller 102 may allocate time slots to the mobile transceiver 104 based on the data rate requirements of the mobile transceiver. The mobile transceiver 104 may indicate in a message to the network controller 102, the number of time slots required for data transmission. Responsive to the indication, the network controller 102 may update the time slot and frequency channel assignment of the mobile transceiver. The network controller 102 then causes the broadcast downlink generator 103 to transmit the updated time slot and frequency channel assignments to the mobile transceiver, over the broadcast downlink. Thus, assigning only the required number of time slots to the mobile transceivers 104 based on the data rate requirements of the mobile transceivers 104 may conserve uplink bandwidth of the telemetry system 100.

In an exemplary embodiment, the network controller 102 may update the frequency channel and time slot assignments of the mobile transceivers 104 after each uplink frame. The constant updates may create gaps or ranges of unassigned time slots in some frequency channels. An unassigned time slot may become unusable if the gap is smaller than the minimum number of contiguous time slots required by the mobile transceiver, or if the unassigned time slot and a simultaneous time slot in the adjacent frequency channel have incompatible channel separation constraints. The presence of unusable time slots results in fragmentation of the available time-frequency space. In order to more effectively utilize the uplink bandwidth and prevent the available time-frequency space from becoming fragmented, the network controller 102 may periodically reassign time slots and frequency channels of certain mobile transceivers 104. In a practical situation, there may be some patients that do not move out of their rooms or beds at all. The time slots and frequency channels assigned to the mobile transceivers 104 attached to such patients may be static, as they may not violate the channel separation constraints at any point of time. The mobile transceivers 104 attached to such patients may be seen as static transceivers. The network controller 102 selects such static transceivers for periodic reassignment of time slots and frequency channels. The network controller 102 may select an optimal number of such static transceivers to make full use of the downlink bandwidth remaining after time slot and frequency channel assignments of moving mobile transceivers 104 are updated. An example process for the periodic reassignment of time slots and frequency channels is described in conjunction with FIG. 11.

Apart from the time slot and frequency channel assignment updates to facilitate the aforementioned functionalities, the telemetry system 100 may also benefit from reduced overall Radio Frequency (RF) transmission level in the hospital premises, thereby decreasing potential interference and mitigating adjacent channel near-far effects. The network controller 102 may thus implement a power control algorithm to control the transmission power of the mobile transceivers 104. The network controller 102 may receive the received signal strength of the mobile transceiver 104 from the distributed receiver 106 with which the mobile transceiver 104 is associated with. The network controller 102 may then compare the received signal strength to a predefine threshold and based on the comparison, may transfer a power control signal intended for that mobile transceiver to broadcast downlink generator 103. The broadcast downlink generator 103 then transmits the power control signal on the broadcast downlink, to the mobile transceiver 104 to adjust the transmission power. A target power level is chosen to maintain a low Bit Error Rate (BER). The transmission power of the mobile transceiver 104 may have a minimum non-zero value to which it can be set. The power control algorithm may also be used to enhance the battery life of the Mobile transceiver 104, by operating the mobile transceiver 104 at the lowest possible power levels, while maintaining a low Bit Error Rate (BER). An example power control algorithm is described in conjunction with FIG. 9.

Measures for reducing the overall RF transmission levels, while maintaining acceptable BER may require an increase in the number of the distributed receivers 106, while decreasing the spacing between the distributed receivers 106. However, this may increase the cost of the telemetry system 100. Therefore, the telemetry system 100 provides for operating a limited number of mobile transceivers 104 at higher-than-specified BER. Such mobile transceivers 104 may transmit additional Forward Error Correction (FEC) data, along with the physiological data and traffic information. FEC data requires additional bandwidth. Therefore, to conserve the uplink bandwidth the telemetry system 100 may allow operation of only a limited number of mobile transceivers 104 at higher-than-specified BER. The network controller 102 receives the BER of the mobile transceiver 104 and compares the BER of the mobile transceiver 104 to a maximum permissible BER. If the BER of the mobile transceiver 104 exceeds the maximum permissible BER, the network controller 102 transfers an error correction enable signal intended for that mobile transceiver 104 to the broadcast downlink generator 103. The broadcast downlink generator 103 then transmits the error correction enable signal to the mobile transceiver 104 on the broadcast downlink. The error correction enable signal enables the FEC scheme in the mobile transceiver. An example process for enabling FEC in the mobile transceiver 104 is described in conjunction with FIG. 10.

In an embodiment of the present invention, the broadcast downlink may also be used for a number of data applications such as, but not limited to, distribution of alerts to one or more of the mobile transceivers 104, download of information to one or more of the mobile transceivers 104, forwarding alerts to the nursing staff, downloading other patient data, firmware updates, and the like.

The mobile transceivers 104 may be two-way communication radio devices equipped with telemeters for monitoring physiological data of the patients to whom the mobile transceivers 104 are attached. The mobile transceivers 104 include a monitoring device such as, but not limited to, sub-diagnostic electrocardiograph (ECG or EKG), electromyograph (EMG), electroencephalograph (EEG), and the like. The mobile transceivers 104 also include two-way communication radios for communicating with network controller 102 and the patient monitoring system 112, through the distributed receivers 106. The mobile transceiver 104 collects physiological data of the patient and formats the physiological data into uplink packets. The mobile transceiver 104 may also compress the physiological data. The mobile transceiver 104 then adds traffic information associated with the mobile transceiver 104 to the uplink packets. In an exemplary embodiment, the mobile transceivers 104 may include a buffer for storing data to be transmitted. The buffer holds compressed and formatted data ready for transmission. The mobile transceiver 104 then modulates and transmits the modulated uplink packets in the assigned frequency channel during the time slots assigned to the mobile transceiver 104. The mobile transceiver 104 receives the time slot and frequency channel assignments from the network controller 102 over the broadcast downlink.

In an exemplary embodiment, the mobile transceivers 104 employ a forward error correction (FEC) scheme that can be selectively enabled by the network controller 102 through the error correction enable signal on the broadcast downlink. The forward error correction scheme may use invertible or complementary codes to generate FEC data. An exemplary FEC scheme includes transmitting over a first frequency the physiological data along with error detection data associated with the physiological data, and transmitting over a second frequency the FEC data associated with the physiological data along with error detection data associated with the FEC data. The physiological data may be recovered by inverting the error detection data associated with the physiological data. If the error detection data associated with the physiological data indicate that the physiological data has been received without errors, the physiological data is directly retrieved and the FEC data is not used. However, the FEC data is used to recover the physiological data, if the error detection data associated with the physiological data indicates that the physiological data has been received with detected errors. In some embodiments, the FEC data is generated using a reduced rate invertible code. In the exemplary FEC scheme, the mobile transceiver 104 transmits the FEC data for every physiological data transmission, without receiving an Automatic Resend Request (ARQ) from the network controller 102. The FEC scheme provides frequency diversity, in that the uplink packet is transmitted on two different frequencies.

The transmission power of the mobile transceiver 104 may also be controlled by the network controller 102, based on received signal strengths at the distributed receivers 106. The mobile transceivers 104 may receive power control signals over the broadcast downlink and adjust the transmission power based on the power control signals.

The telemetry system 100 also includes the patient monitoring system 112. The patient monitoring system 112 is responsible for collecting and displaying the physiological data of the patients transmitted by the mobile transceivers 104, on a Graphic User Interface (GUI), in a human readable form. The physiological data may be displayed in the form of graphs, waveforms, and the like. The patient monitoring system 112 may also generate warning messages and alerts, based on a predefined logic. The patient monitoring system 112 receives the physiological data of the patients from the distributed receivers 106, along with the mobile transceiver identifier of the mobile transceiver 104 that sent it. The patient monitoring system 112 may then decode the physiological data, and display it.

Figure 2:
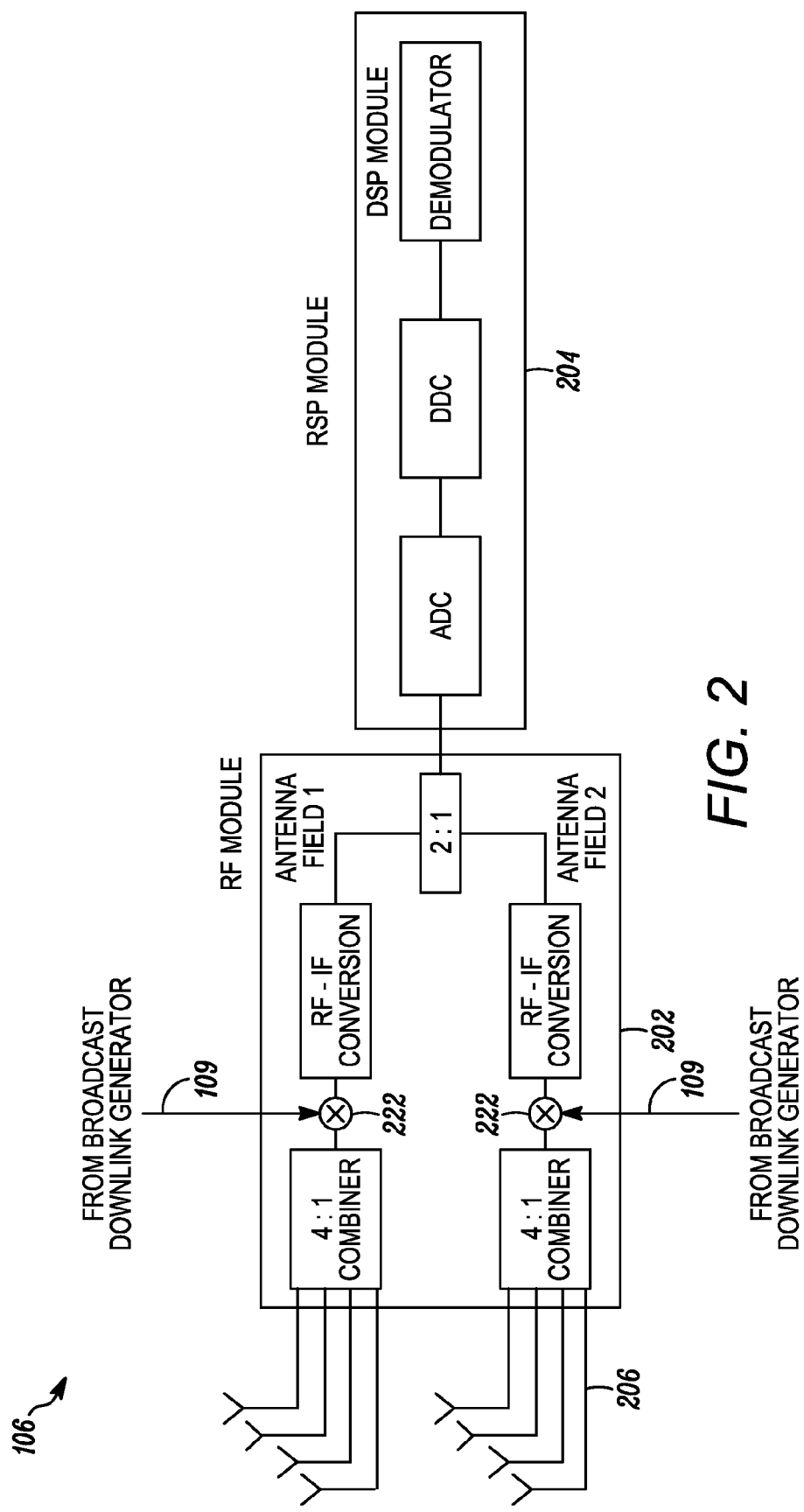
FIG. 2 illustrates a simplified block diagram of a distributed receiver, according to one embodiment.

FIG. 2 is a simplified block diagram of an exemplary distributed receiver 106 operable in the telemetry system 100. Each distributed receiver 106 demodulates specific frequency channels allocated from the total uplink bandwidth. The distributed receiver 106 includes one or more receive front-end (RFE) modules 202, one or more receive signal processors (RSP) 204 and one or more antennas 206. The antennas 206 transmit the broadcast downlink and receive uplink packets to and from the mobile transceivers 104 respectively.

The RFE modules 202 condition the received broadcast downlink for transmission through the antennas. The RFE module 202 may receive the broadcast downlink from the broadcast downlink generator over link 109. Link 109 may be any suitable RF transmission medium such as, but not limited to, a fiber optic cable, a broadband co-axial cable, and the like. The RFE module 202 may couple the broadcast downlink to the antennas using a circulator 222. In some embodiments, other devices for coupling RF signals may be used in place of circulator 222, for example, mixers, adders, switches, and the like. In some other embodiments, the RFE module 202 may receive a baseband broadcast downlink, filter, synchronize and up-convert the broadcast downlink, and provide it to the antennas for transmission to the mobile transceivers 104. The RFE modules 202 may also measure the signal strength of each of the received uplink transmissions and associate the signal strengths with the mobile transceiver identifiers in the respective uplink transmissions. The RFE modules 202 also condition the received uplink transmissions for processing in the RSP modules 204. The RFE module 202 re-modulates the signals of separate antenna fields to separate Intermediate Frequencies (IF) and combines the separate intermediate frequencies to a composite analog IF signal. The analog IF signal of the RFE module 202 is then fed to the RSP module 204 for further processing.

The RSP module 204 converts the composite analog IF signals from the RFE module 202 into uplink packets using a high-speed analog to digital converter (ADC). The uplink packets may then be filtered and decimated in several stages for further processing by a Digital Signal Processor (DSP). The DSP demodulates the uplink packets and detects errors in the uplink packets. The DSP then segregates the uplink packets into traffic information associated with the individual mobile transceivers 104 and the physiological data of the patients. The DSP may identify the current time slot and frequency channel assignments of the mobile transceivers 104, based on the mobile transceiver identifier. The DSP identifies that the time slots in the frequency channel during which the mobile transceiver identifier was received, are in use by the mobile transceiver 104. The DSP may also aid in determining the presence of the mobile transceiver 104 i.e., in which of the various coverage zones 110 a particular mobile transceiver 104 resides. The DSP may share the measured signal strength of the uplink transmissions, and the associated mobile transceiver identifier in the respective uplink transmissions with other distributed receivers 106, to determine which one of the distributed receivers 106 has the best reception of a particular mobile transceiver 104, and continue reception of uplink transmissions from that mobile transceiver 104. The DSP may communicate with the DSPs of other distributed receivers 106 through network 108. The DSP may append traffic information associated with the distributed receiver 106 to traffic information associated with the mobile transceivers 104. The DSP then forwards the physiological data to the patient monitoring system 112 and traffic information to the network controller 102, over the network 108. The DSP may also transmit the uplink packet error statistics of the mobile transceivers 104 to the network controller 102. The DSP may either include the packet error statistics in traffic information or directly send an error report to the network controller 102.

In an exemplary embodiment, the RFE module 202 may support multiple sets of combined antennas, each demodulating the frequency channels allocated to the distributed receiver 106. Each set of coherently combined antennas form an antenna field. The antenna field may be defined as a region in space in which a mobile transceiver 104 may transmit or receive signals to or from the distributed receiver 106, while maintaining a satisfactory Bit Error Rate (BER) and utilizing a nominal transmission power. In such an embodiment, the composite analog IF signal contains multiple images of each of the frequency channels, one from each antenna field of the RFE module 202. The RSP module 204 may demodulate some or all of these images of the frequency channels. The RSP module 204 may then select the uplink packets that have the least number of errors. Such an uplink demodulation scheme provides spatial diversity on the basis of packet-by-packet selection, using error detection data present in every uplink packet.

In the case that the mobile transceiver 104 has FEC enabled, the ability of the RSP module 204 to demodulate multiple images of the frequency channel of the mobile transceiver 104, provides frequency and spatial diversity respectively, in that RSP module 204 demodulates multiple different images of two different frequency channels.

Figure 3:
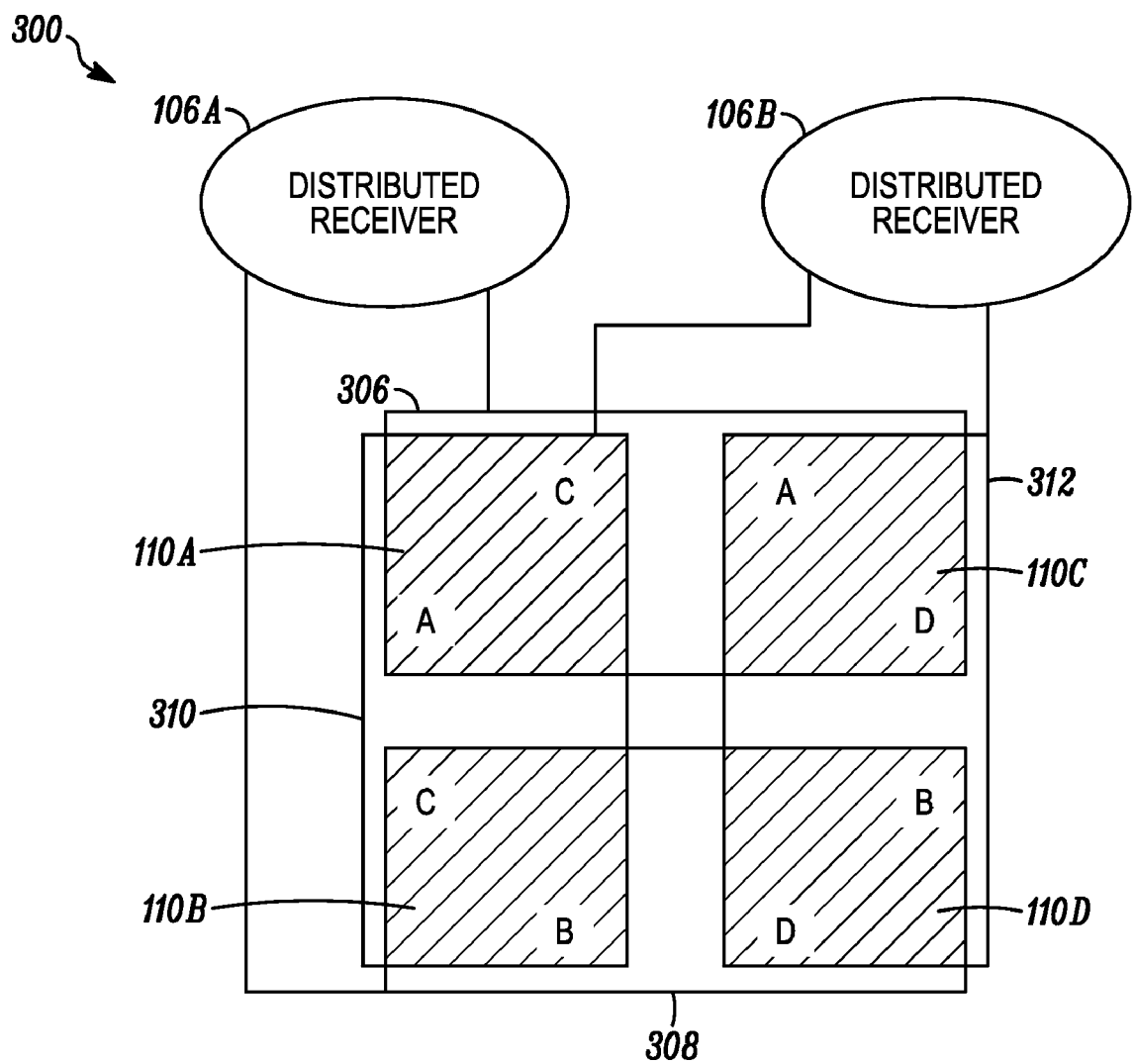
FIG. 3 illustrates exemplary coverage zones of the distributed receiver in which mobile transceivers may operate, according to one embodiment.

FIG. 3 is an illustration of exemplary coverage zones 110 in which the mobile transceivers 104 may operate. The shape of the coverage zones 110 illustrated in FIG. 3 are for representation only. FIG. 3 illustrates two distributed receivers 106A and 106B, described in conjunction with FIG. 2. The distributed receiver 106A operates antenna field 306 and antenna field 308, formed by sets A and B, respectively, of coherently combined antennas. The distributed receiver 106B operates antenna field 310 and antenna field 312, formed by sets C and D, respectively, of coherently combined antennas.

The shaded regions 110A, 110B, 110C, 110D in FIG. 3 represent the coverage zones 110 described in conjunction with various embodiments. The coverage zones 110 may be defined as regions in space, where two or more antenna fields overlap. All coverage zones 110 having at least one common antenna field are defined as adjacent zones. For example, for the coverage zone 110A, the coverage zones 110B and 110C are the adjacent zones. The coverage zone 110A shares the antenna field 310 with the coverage zone 110B, and the antenna field 306 with the coverage zone 110C. The coverage zones 110 that are located far apart in space may support frequency re-use. Such coverage zones 110 may be called frequency re-use zones.

The mobile transceivers 104 may move from one antenna field to another, from the coverage zone of one distributed receiver 106 to that of another distributed receiver 106 and from one frequency re-use zone to another. Further, the distributed receivers 106 may communicate with each other to determine which distributed receiver 106 is to receive transmissions from which of the mobile transceivers 104. The distributed receivers 106 may measure the received signal strengths of all received uplink transmissions and associate the received signal strengths with the mobile transceiver identifiers in the respective uplink transmissions. The distributed receivers 106 may then share with the other distributed receivers 106 the received signal strengths and the associated mobile transceiver identifiers, to determine which one of the distributed receivers 106 has the best reception of a particular mobile transceiver 104, and continue reception of uplink transmissions from that mobile transceiver 104. In one embodiment, each distributed receiver 106 has computational resources permitting demodulation of every time/frequency slot. In another embodiment, a distributed receiver 106 has computational resources sufficient for demodulation of only a subset of time/frequency slots. The network controller 102 may update the time slot and frequency channel assignments of the mobile transceivers 104 when the mobile transceivers 104 move between antenna field coverage zones 110. The network controller 102 must minimize interference between the mobile transceivers 104 while updating the time slot and frequency channel assignments of the mobile transceivers 104. The network controller 102 updates the time slot assignments and frequency channel assignments of the mobile transceivers 104 taking into account the time slot assignments and frequency channel assignments of other mobile transceivers 104 in the same or adjacent coverage zones 110. The network controller 102 may minimize interference by maintaining certain channel separation between the mobile transceivers 104 transmitting simultaneously in the various coverage zones 110. The network controller 102 may utilize a constraint map defining channel separation parameters for simultaneous uplink transmissions, while updating the time slot assignments and frequency channel assignment of the mobile transceivers 104, to minimize interference.

Figures 4A, 4B:
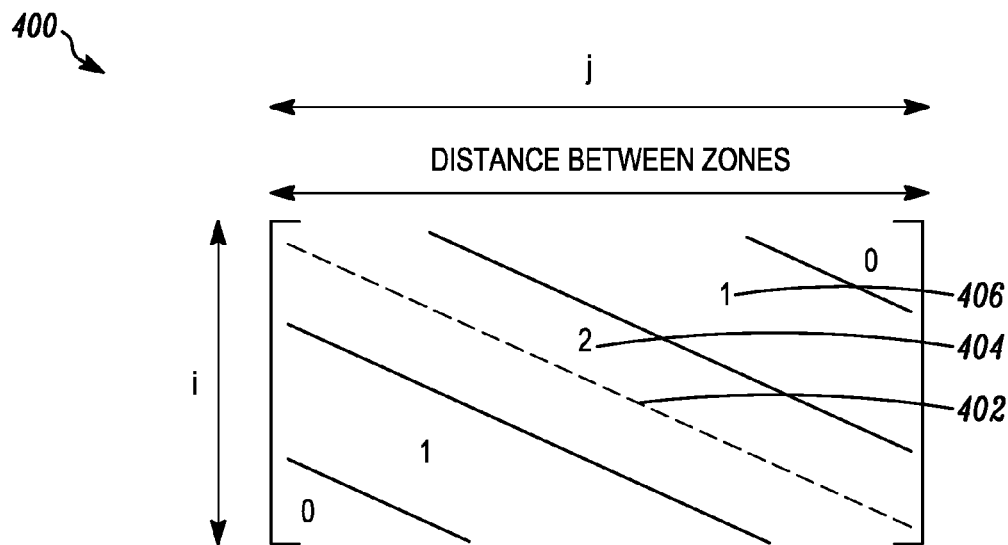
FIGS. 4A and 4B illustrate exemplary channel separation constraint maps, according to one embodiment.

FIG. 4A illustrates an exemplary constraint map 400. In an exemplary embodiment, the constraint map 400 is a matrix defining frequency channel separation parameters for simultaneous uplink transmissions. Each entry in the constraint map 400 may represent a channel separation required between mobile transceivers 104 transmitting simultaneously. The $i,j^{th}$ entry may be the channel separation required between a mobile transceiver 104 in zone 'i' transmitting simultaneously with a mobile transceiver 104 in zone 'j'.

The constraint map 400 defines three types of channel separation parameters for simultaneous uplink transmissions. Co-site constraints 402 define channel separation parameters for the mobile transceivers 104 transmitting simultaneously in the same coverage zone 110. Adjacent zone constraints 404 define channel separation parameters for the mobile transceivers 104 transmitting simultaneously in adjacent zones. Co-channel constraints 406 ensure that the mobile transceivers 104 in coverage zones not sufficiently well-separated from each other do not occupy the same frequency channel in the same time slot. Co-channel constraints 406 prohibit a channel from being used by two mobile transceivers 104 unless the mobile transceivers 104 are well separated from each other in space.

In an exemplary embodiment, the difference in the index (row or column number) is roughly indicative of the distance between coverage zones 110. In such a case, the co-site constraints may be located on the main diagonal, the adjacent zone constraints may be near the main diagonal, and the co-channel constraints may be located elsewhere in the constraint map 400. Frequency re-use may occur only between widely separated coverage zones 110 only. The coverage zones 110 capable of frequency re-use are indicated by a lack of constraints and tend to be at entries farther from the main diagonal.

In an exemplary embodiment, the constraint map 400 may be defined at start-up for the telemetry system 100, since the constraint map 400 may be static for a given installation. The constraint map 400 may be defined by employing a start-up mode. During the start-up mode, a mobile transceiver 104 is moved around the hospital facility and the received power is measured at every distributed receiver 106 for every mobile transceiver 104 position. The constraint map 400 may then be defined using the measured power levels. Based on the measured power levels, and the amount of signal coupling between each antenna of each distributed receiver 106 and the mobile transceiver 104, the number of frequency channels of separation required for mobile transceivers 104 in the same or adjacent coverage zones is determined. Path loss of the mobile transceiver 104 signals may also be factored in defining the constraint matrix 400. In other embodiments, the constraint map 400 may be dynamically updated in normal operation of the telemetry system 100.

FIG. 4B illustrates an exemplary constraint map 410 with exemplary channel separation parameters for nine coverage zones 110. For example, a mobile transceiver 104 in coverage zone C must be separated from another mobile transceiver 104 in coverage zone A by two frequency channels, or from a mobile transceiver 104 in coverage zone F by one frequency channel. A mobile transceiver 104 in coverage zone C may use the same frequency channel as another mobile transceiver 104 in coverage zones G or H.

FIGS. 5 and 6 illustrate exemplary packet structures of the broadcast downlink burst 502 and the uplink burst 602 respectively. The broadcast downlink burst 502 is a series of broadcast downlink packets transmitted by the network controller 102 in a single downlink frame. Similarly, the uplink burst 602 is a series of uplink packets transmitted by the mobile transceiver 104 in a single uplink frame.

FIG. 5 illustrates an exemplary broadcast downlink burst 502. The broadcast downlink burst 502 includes the updated time slot and frequency channel assignments for the mobile transceivers 104. The broadcast downlink burst 502 may also keep a mobile transceiver 104 in synchronization with the network controller 102. The mobile transceiver 104 may synchronize the slot clock with the slot clock of the telemetry system 100 using the preamble of the downlink burst 502. The broadcast downlink burst 502 may also contain an information packet that will indicate the current phase of the frame clock of the telemetry system 100, to the mobile transceiver 104.

The broadcast downlink burst 502 may have a preamble, an information packet and one or more control packets. The information packet and the control packets have independent error detection bits. The information packet may give the slot number within the current frame in which the burst began. The control packet contains commands for the mobile transceivers 104. The commands may be for the time slot assignments and the frequency channel assignments for uplink burst 602 transmission, power control, enabling FEC, and the like. The control packet may contain the mobile transceiver identifier of the mobile transceiver 104 for which the control packet is intended. The mobile transceivers 104 that receive the broadcast downlink burst 502 may have to demodulate all control packets in the broadcast downlink burst 502 to identify the mobile transceiver identifier in the control packet. The mobile transceiver 104 may execute the commands included in the control packet if the mobile transceiver identifier of the mobile transceiver 104 matches the mobile transceiver identifier in the control packet. In an exemplary embodiment, a downlink burst 502 may include only one control packet for a given mobile transceiver 104. The control packets may be broadcast using two different frequencies, providing frequency diversity similar to the uplink packets. The size of the control packet may be such that the same forward error correction scheme as employed for the uplink packets may be used for the broadcast downlink packets also.

In an exemplary embodiment of the present invention, the preamble may be 160 bits long, the information packet may be 108 bits long and the control packet may be 108 bits long, with both, the information packet and the control packet followed by 16 bits of CRC data.

FIG. 6 illustrates an exemplary uplink burst 602. The uplink burst 602 includes a preamble, one or more information packets, and one or more data packets. The information packets and the control packets have independent error detection bits. The information packets may contain information identifying the type of data in the burst. The information packets may also contain traffic information associated with the mobile transceiver such as buffer state of the mobile transceiver. In an exemplary embodiment, two information packets may be present in the uplink burst 602, the second of which may be a simple repetition of the first, for reliability. The data packets include traffic information associated with the mobile transceiver 104 such as, but not limited to, the mobile transceiver identifier, and the number of data packets actually transmitted by the mobile transceiver 104. The maximum uplink burst 602 length may be varied by the network controller 102, to change uplink data rate. The total uplink burst 602 length may vary in multiples of the time slot duration, and not in multiples of the packet duration.

In an exemplary embodiment of the present invention, the preamble may be 160 bits long, the information packet may be 108 bits long and the data packet may be 108 bits long, with both, the information packet and the data packet followed by 16 bits of CRC data.

Figure 7:
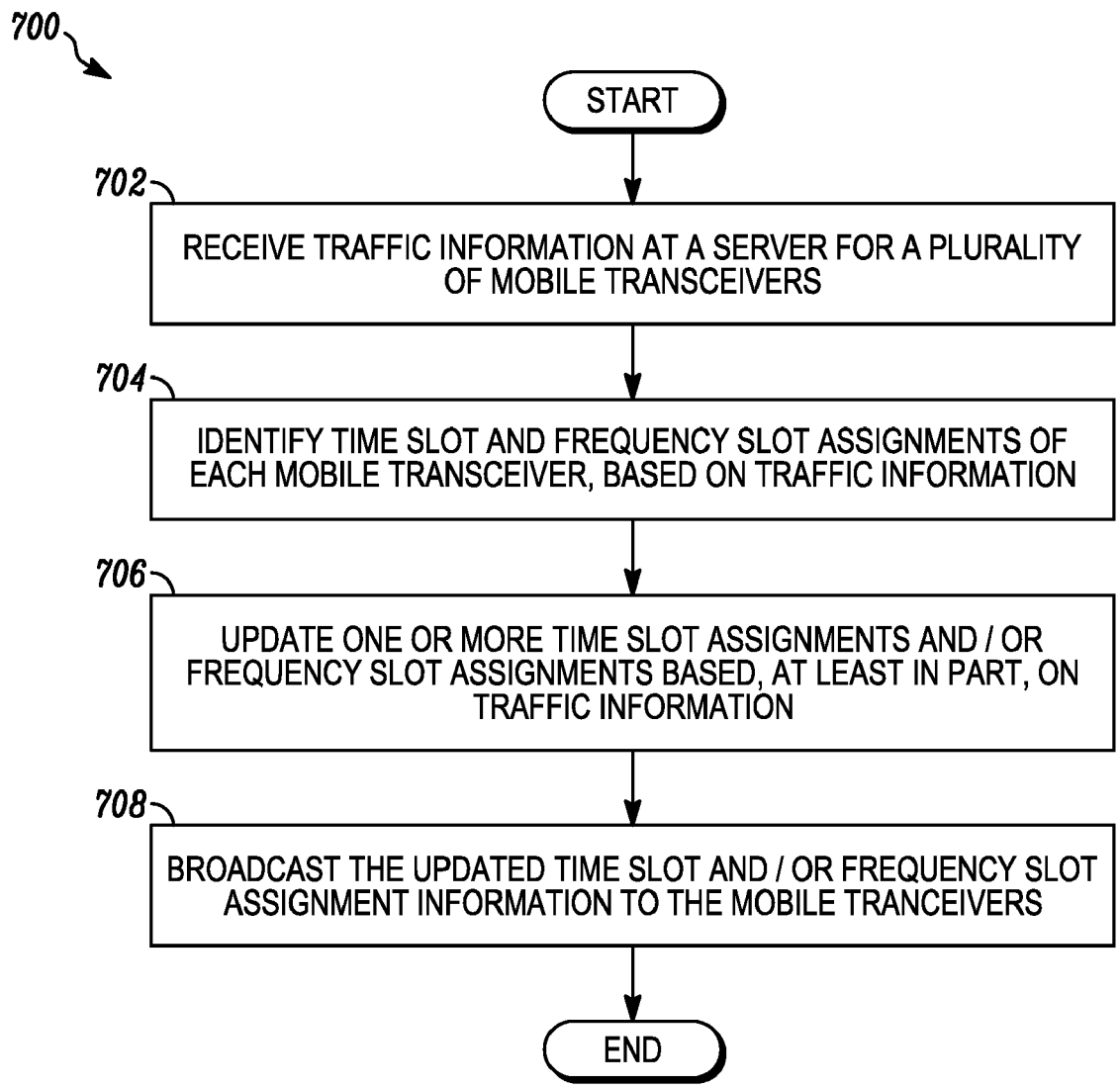
FIG. 7 is a flowchart illustrating an exemplary process for reuse of radio resources in a medical telemetry network, according to one embodiment.

FIG. 7 is a flowchart of an exemplary process for reusing radio resources in a centralized medical telemetry network such as the telemetry system 100.

At step 702, the network controller 102 receives traffic information for a plurality of mobile transceivers 104, from a plurality of distributed receivers 106. As described in conjunction with FIG. 3, the mobile transceivers 104 operate in coverage zones 110. The coverage zones 110 are regions where two or more antenna fields of the distributed receivers 106 overlap. As described in conjunction with FIG. 2, all the distributed receivers 106, which receive the uplink transmissions from the mobile transceiver 104, forward the traffic information to the network controller 102. Traffic information includes the number of mobile transceivers 104 in communication with each of a plurality of distributed receivers 106, mobile transceiver identifiers of the mobile transceivers 104, buffer state of the mobile transceivers 104, and presence of the mobile transceivers 104 in coverage zones of the distributed receivers 106.

At step 704, the network controller 102 identifies time slot assignments and frequency channel assignments of the mobile transceivers 104 based on traffic information. The network controller 102 may use traffic information associated with the mobile transceiver 104 such as, but not limited to, the mobile transceiver identifier of the mobile transceiver 104.

At step 706, the network controller 102 updates one or more time slot assignments and/or one or more frequency channel assignments based on traffic information. The network controller 102 also takes into account the channel separation parameters, to mitigate co-channel interference, adjacent zone interference and co-site interference, specified in the constraint map.

At step 708, the network controller 102 broadcasts the updated instances of the time slot assignments and updated instances of frequency channel assignments. The network controller 102 uses the broadcast downlink to broadcast the updates. The network controller 102 transmits only the changes to a mobile transmitter time slot and/or frequency channel assignment in order to conserve broadcast downlink bandwidth.

Figure 8:
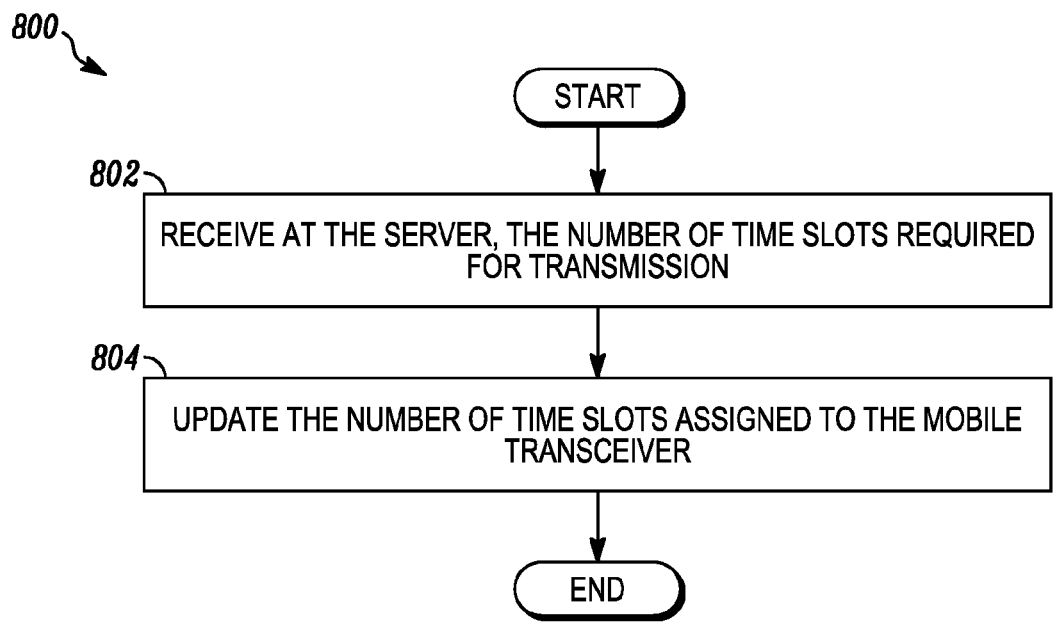
FIG. 8 is a flowchart illustrating an exemplary process for varying the uplink transmission rate of a mobile transceiver, according to one embodiment.

FIG. 8 is a flowchart of an exemplary process for varying the uplink transmission rate of a mobile transceiver 104.

At step 802, the network controller 102 receives the number of time slots required by each of the plurality of mobile transceivers 104. Different types of patient telemeters may require different data rates. Further, different mobile transceivers 104 may employ different compression rates. The mobile transceivers 104 may transmit the number of time slots required based on the type of telemeter connected.

At step 804, the network controller 102 updates the number of time slots assigned to one or more of the plurality of mobile transceivers based on the number of time slots required. In various embodiments, the mobile transceivers 104 indicate the number of time slots required, taking into consideration, changes to the amount of data to be transmitted, compression of the data to be transmitted, or any other increases in the volume of data to be transmitted.

Figure 9:
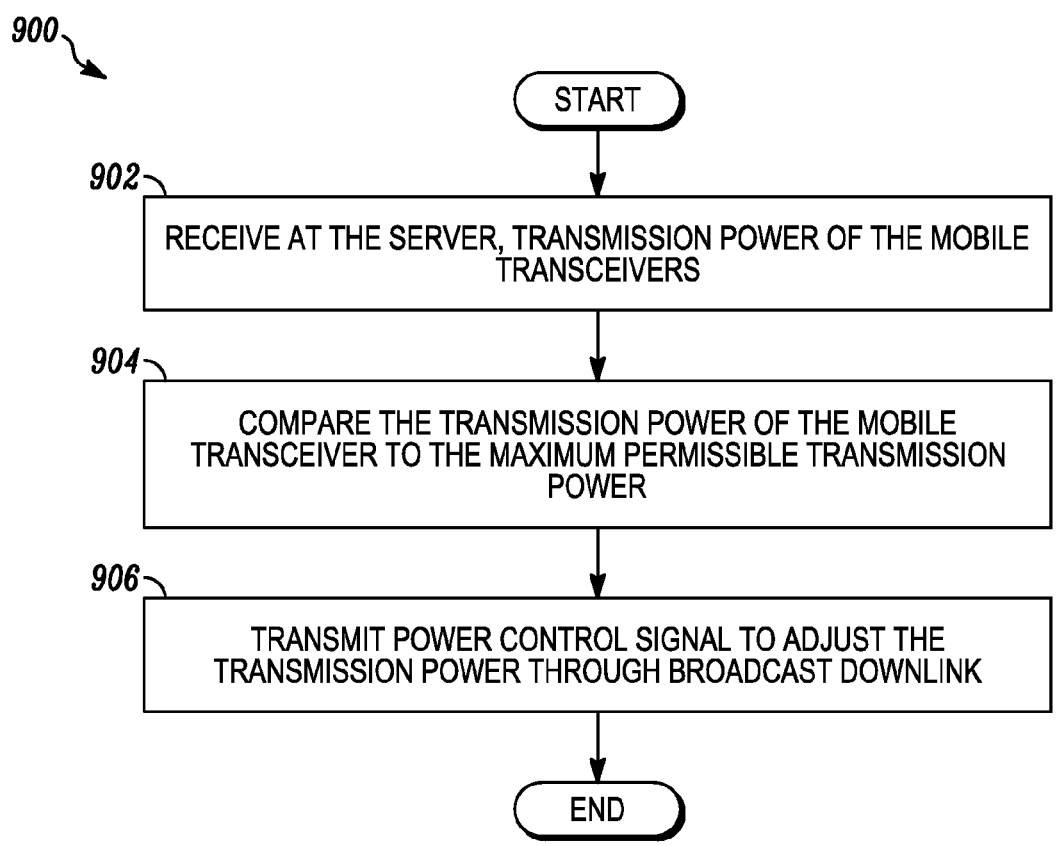
FIG. 9 is a flowchart illustrating an exemplary process for varying transmission power of a mobile transceiver, according to one embodiment.

FIG. 9 is a flowchart of an exemplary process for varying transmission power of a mobile transceiver 104. Power control will lower the radiated power of the individual mobile transceivers 104 to reduce interference, subject to maintaining a low Bit Error Rate (BER) in the uplink packets.

At step 902, the network controller 102 collects the received power of each of the plurality of mobile transceivers. The distributed receivers 106 may measure the received signal strength of the mobile transceivers 104. In an exemplary embodiment, two received signal strength measurements may be made for each mobile transceiver 104 at two different distributed receivers 106. The power control algorithm may be setup to operate with respect to that Distributed receiver at which the received signal is strongest. The distributed receivers 106 may then transmit the measured power levels to the network controller 102.

At step 904, the network controller 102 compares the transmission power of each of the plurality of mobile transceivers to a maximum permissible transmission power. The maximum permissible power may be set depending on the requirements of the installation. In an exemplary embodiment, the maximum permissible power that may be radiated by a mobile transceiver 104 may be fixed at +10 dBm.

At step 906, the network controller 102 transmits a power control signal to adjust the transmission power of one or more of the plurality of mobile transceivers responsive to the comparison. The network controller 102 may transmit the power control signal through the broadcast downlink to the mobile transceiver 104. The mobile transceiver 104 may then adjust the transmission power to a new value, as specified by the network controller 102.

Figure 10:
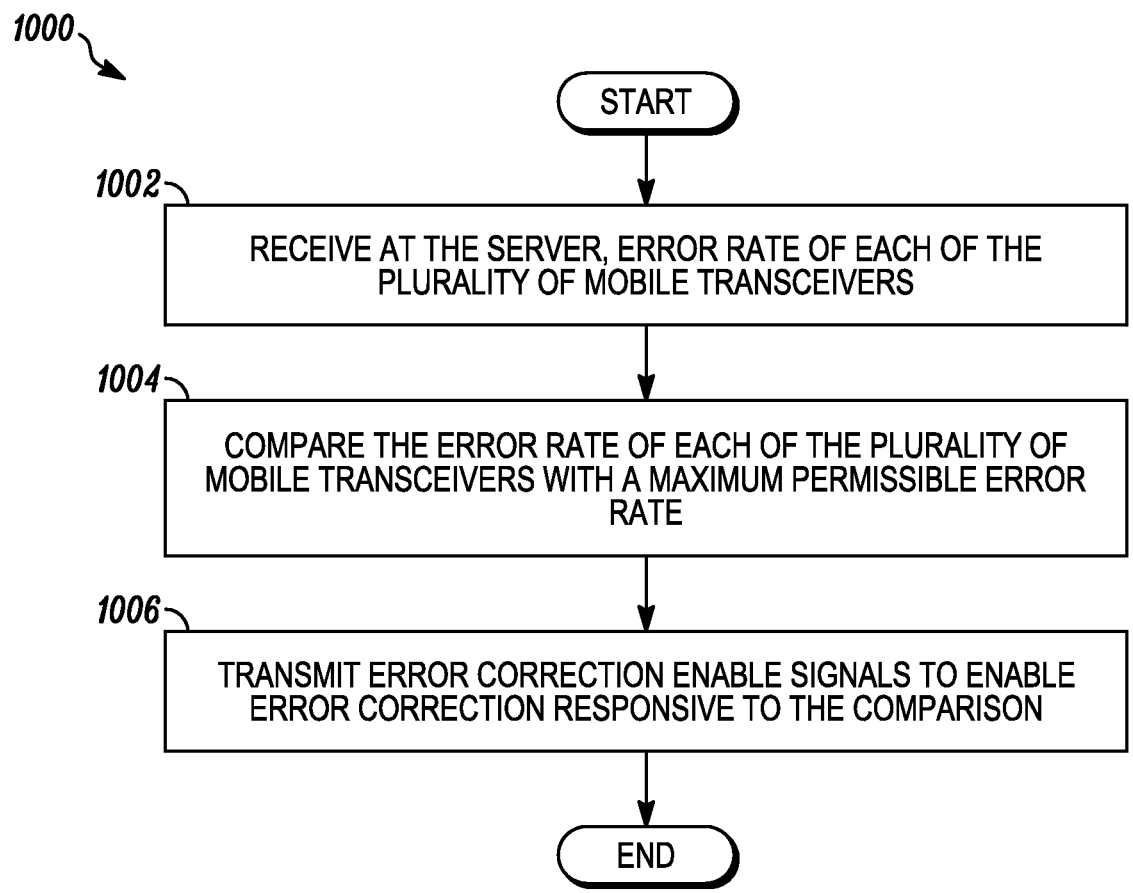
FIG. 10 is a flowchart illustrating an exemplary process for selectively enabling forward error correction on mobile transceivers, according to one embodiment.

FIG. 10 is a flowchart of an exemplary process for selectively enabling forward error correction on mobile transceivers 102.

At step 1002, the network controller 102 receives the error rate of each of the plurality of mobile transceivers 104. The distributed receivers 106 detect errors in uplink transmissions from mobile transceivers 104, using the CRC bits in the uplink transmissions. The distributed receivers 106 may then transmit the error statistics of the mobile transceivers 104 to the network controller 102.

At step 1004, the network controller 102 compares the error rate of each of the plurality of mobile transceivers with a maximum permissible error rate. The maximum permissible error rate may be decided at the time of installation and may be dependent on the requirements of the method.

At step 1006, the network controller 102 transmits error correction enable signals to enable error correction on one or more of the plurality of mobile transceivers responsive to the comparison. If the error rate of the mobile transceiver 104 approaches or exceeds the maximum permissible error rate, the network controller 102 transmits error correction enable signals through the broadcast downlink to the mobile transceivers 104.

The FEC scheme may be enabled only when required, thus preserving uplink bandwidth, while ensuring accuracy of patient's physiological data. The network controller 102 may enable or disable the FEC scheme on the mobile transceiver 104 by transmitting respective control signals over the broadcast downlink. The network controller 102 may also update the number of time slots assigned to the mobile transceivers 104 to allow transmission of error correction data.

Figure 11:
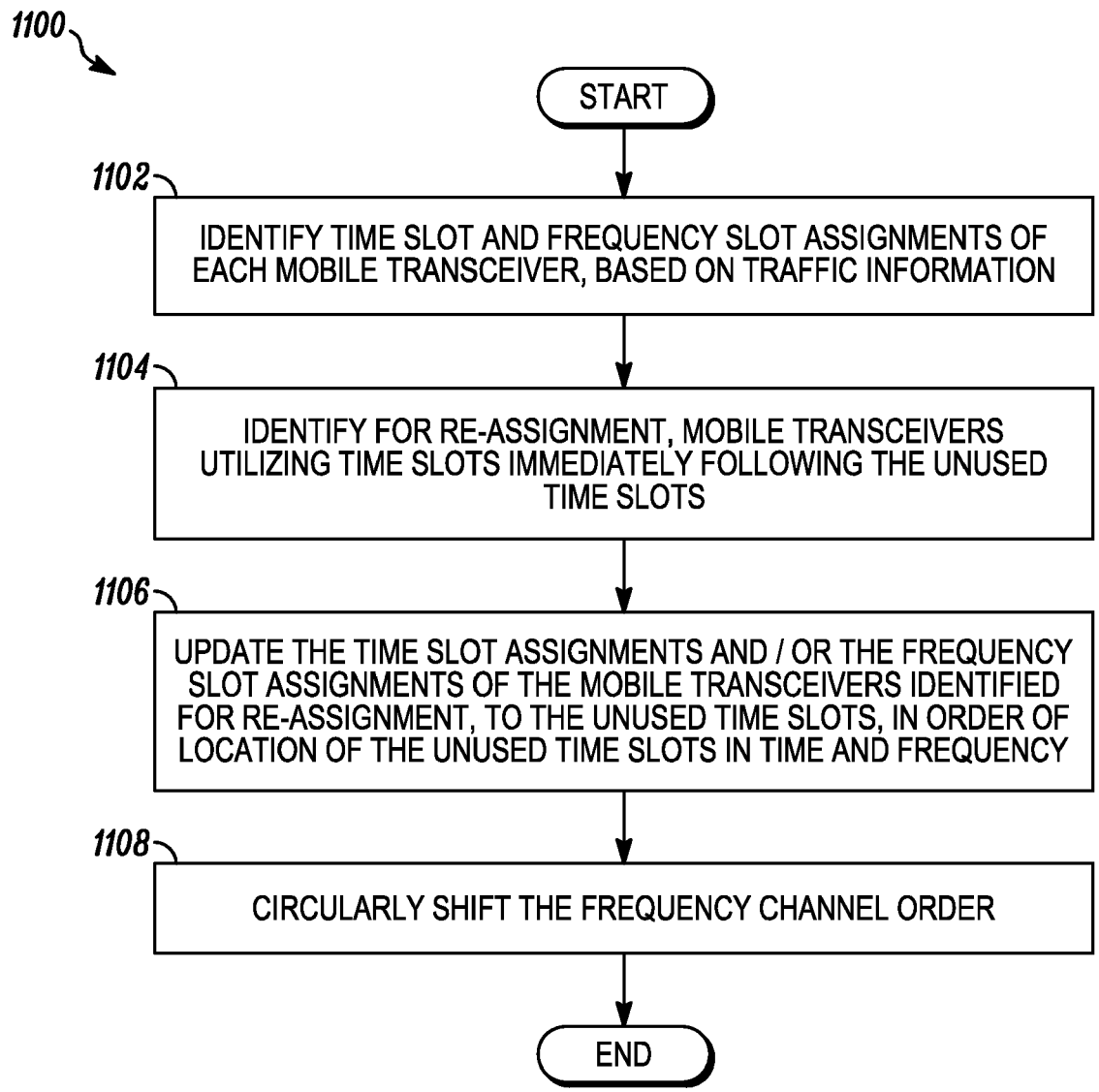
FIG. 11 is a flowchart illustrating an exemplary periodic reassignment of time slots and frequency channels, according to one embodiment.

FIG. 11 is a flowchart of an exemplary process for periodic reassignment of time slots and frequency channels for optimal bandwidth utilization. The network controller 102 may define a slot map, which is a list of time slots, in the order in which they are to be assigned. The network controller 102 periodically tags each time slot in the slot map with an identification of the coverage zone 110 in which the mobile transceiver 104 may transmit during that time slot. An exemplary slot map is illustrated in FIG. 12A and FIG. 12B.

At step 1102, the network controller 102 identifies unused time slots in each of a plurality of frequency channels. The network controller 102 accesses the slot map, and identifies the unused time slots in each of the plurality of frequency channels.

At step 1104, the network controller 102 identifies for re-assignment, mobile transceivers 104 transmitting in time slots immediately following the unused time slots.

At step 1106, the network controller 102 updates the time slot assignments and/or the frequency channel assignments of the mobile transceivers 104 identified for re-assignment, to the unused time slots, in order of location of the unused time slots in time and frequency. If step 1106 runs for a long time, the slot map may become static. In particular, it is possible for the mobile transceiver 104 transmitting an uplink burst 602 following a gap to have nowhere to which it could be reassigned. This may happen if the mobile transceiver 104 cannot occupy the gap because of adjacent channel or co-site constraints, and it may result in gaps remaining unusable until patient mobility changes the channel separation constraints.

At step 1108, the network controller 102 circularly shifts the frequency channel order. Step 1108 changes the frequency channel order on a periodic basis, while it accesses the channel list as a circular buffer. Since, burst reassignments are made to the first unassigned gap on the slot map first, circularly shifting the frequency channel order changes the region of the slot map into which the algorithm attempts to reassign the mobile transceivers 104. Thus, the mobile transceiver 104 transmitting in an uplink burst 602, that follows a gap, may be moved after a relatively short time.

FIG. 12A illustrates an exemplary slot map. A slot map is a tabular representation of slots assigned to coverage zones in order of time slots and frequency channels. The slot map 1200A illustrates time slot and frequency channel assignments adhering to the constraint map 410 of FIG. 4B. The slot map 1200A illustrates a segment of eight time slots for five consecutive frequency channels. The slot map has two bursts of unassigned time slots—the first which is six time slots long in frequency channel F2, and the second which is three time slots long in frequency channel F4.

Consider an exemplary application such as EKG telemetry, where the minimum uplink burst 602 size required to transmit a complete EKG waveform may be six slots long. The unassigned burst in frequency channel F4 is too short for assignment to a mobile transceiver 104, and is therefore unusable.

On the other hand, the unassigned burst in frequency channel F2 is equal to the minimum uplink burst 602 size required to transmit a complete EKG waveform, and may be directly assigned to a mobile transceiver 104. Eight time slots in frequency channel F1 are assigned to the mobile transceiver 104 in coverage zone G. However, due to the co-site constrains 402 and the adjacent zone constraints 404, no mobile transceiver 104 in zones E, G or H can be assigned the unused slots in frequency channel F2. Further, frequency channel F3 has two separate uplink burst 602s overlapping the six unassigned time slots in frequency channel F2. The first uplink burst 602 is assigned to the mobile transceiver 104 in the coverage zone F and the second burst is assigned to the mobile transceiver 104 in the coverage zone C. No mobile transceiver 104 in coverage zones B, D, E, F or I may be assigned the unassigned time slots because of the channel separation constraints related to coverage zone F, and no mobile transceiver 104 in coverage zones A, C or D may be assigned the unassigned time slots because of the channel separation constraints related to zone C. Considering the union of the aforementioned channel separation constraints the unassigned time slots in frequency channel F2 are unusable in any zone. Therefore, as described in conjunction with FIG. 11, the network controller 102 identifies mobile transceivers 104 in coverage zone I for reassignment. In an exemplary scenario, the network controller 102 reassigns the mobile transceiver 104 transmitting in time slots T8 onwards on frequency channel F2 to a separate channel in the slot map 1200A. Thus, an even larger gap is created in frequency channel F2, due to the reassignment.

After a predetermined time interval, the network controller 102 circularly shifts the order of the frequency channels in the slot map 1200A. Circularly shifting the slot map involves changing the order of the frequency channels in a circular manner.

FIG. 12B illustrates a slot map 1200B, which is the circularly shifted version of the slot map 1200A. The slot map 1200B illustrates the frequency channel order for periodic reassignments as F4, F5, F1, F2, and F3. The three unassigned time slots in frequency channel F4 may now be the first to be reassigned. The network controller 102 identifies the mobile transceivers 104 in the coverage zone E for reassignment. In an exemplary scenario, the network controller 102 updates time slot and frequency channel assignment of the mobile transceiver 104, transmitting in time slots T6 onwards on frequency channel F4, to the unassigned time slots T3-T6 in frequency channel F4. In other words, the network controller 102 shifts the time slots T6 onwards into the gap, thus closing up the gap.

Figure 13:
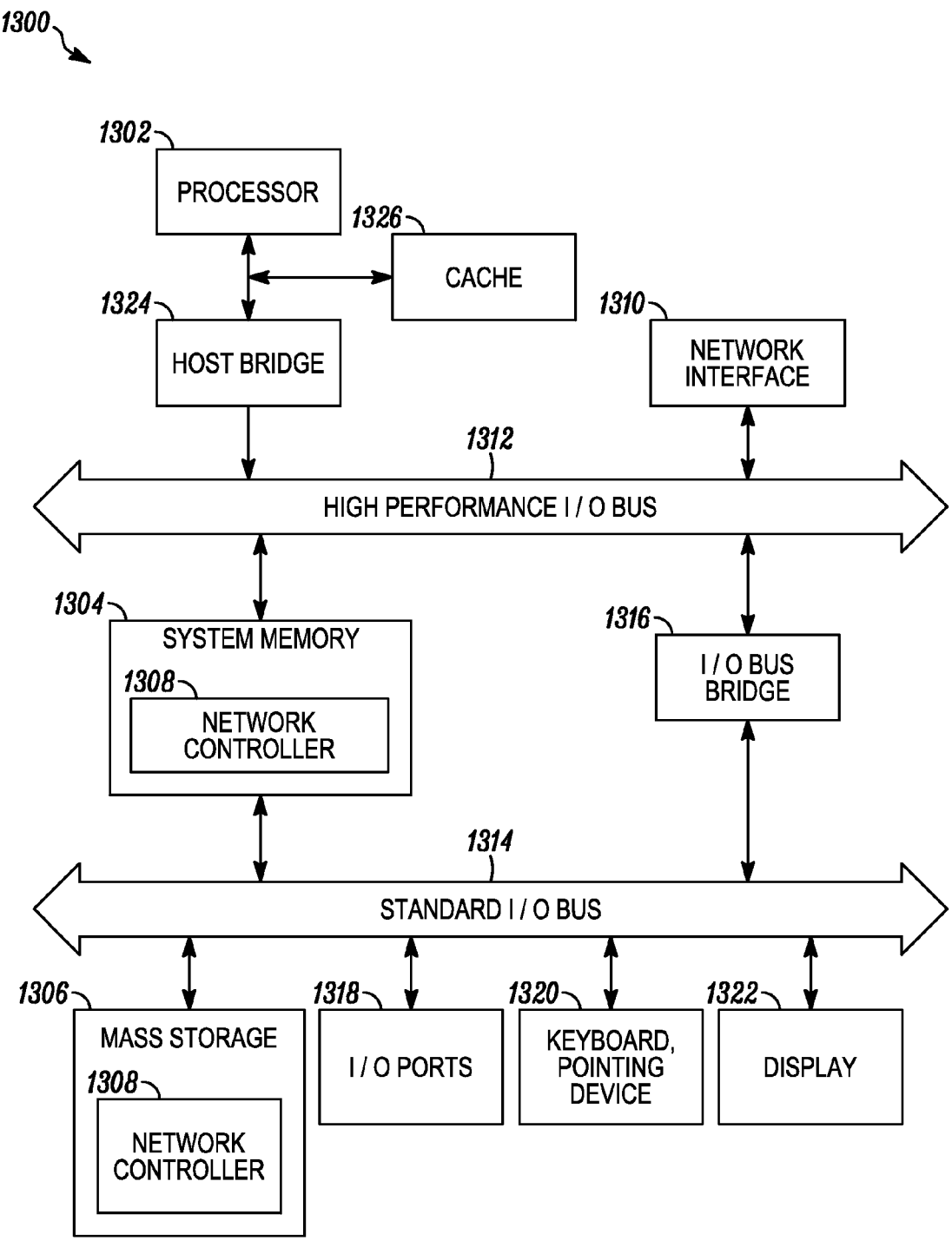
FIG. 13 is an exemplary computer system for implementing the network controller, according to one embodiment.

FIG. 13 illustrates an example hardware system 1300 to implement the network controller 102 according to one embodiment. Hardware system 1300 includes at least one processor 1302, a system memory 1304, and mass storage 1306. The system memory 1304 has stored therein one or more application software, programming instructions 1308 for implementing the network controller 102, an operating system and drivers directed to the functions described herein. Mass storage 1306 provides permanent storage for the data and programming instructions 1308 for the network controller 102, whereas system memory 1304 (e.g., DRAM) provides temporary storage for the data and programming instructions when executed by processor 1302. The process flow of the programming instructions 1308 for the network controller 102 is described in detail in conjunction with FIGS. 7 through 11. In on embodiment, the constraint maps 400 and/or 410 may reside in mass storage 1306. A network/communication interface 1310 provides communication between hardware system 1300 and any of a wide range of networks, such as an Ethernet (e.g., IEEE 802.3) network, etc. Additionally, hardware system 1300 includes a high performance input/output (I/O) bus 1312 and a standard I/O bus 1314. System memory 1304 and network/communication interface 1310 are coupled to bus 1312. Mass storage 1306 is coupled to bus 1314. I/O Bus Bridge 1316 couples the two buses 1312 and 1314 to each other.

In one embodiment, processes 700, 800, 900, 1000, and 1100 described herein are implemented as a series of software routines run by hardware system 1300. These software routines comprise a plurality or series of instructions to be executed by a processor in a hardware system, such as processor 1302. Initially, the series of instructions are stored on a storage device, such as mass storage 1306. However, the series of instructions can be stored on any suitable storage medium, such as a diskette, CD-ROM, ROM, EEPROM, DVD, Blu-ray disk, etc. Furthermore, the series of instructions need not be stored locally, and could be received from a remote storage device, such as server on a network, via network/communication interface 1310. The instructions are copied from the storage device, such as mass storage 1306, into system memory 1304 and then accessed and executed by processor 1302.

In one embodiment, hardware system 1300 may also include I/O ports 1318, a keyboard and pointing device 1320, a display 1322 coupled to bus 1312. I/O ports 1318 are one or more serial and/or parallel communication ports that provide communication between additional peripheral devices, which may be coupled to hardware system 1300. A host bridge 1324 couples processor 1302 to high performance I/O interface 1310. Hardware system 1300 may further include video memory (not shown) and a display device coupled to the video memory. Collectively, these elements are intended to represent a broad category of computer hardware systems, including but not limited to general purpose computer systems based on the x86-compatible processors manufactured by Intel Corporation of Santa Clara, Calif., and the x86-compatible processors manufactured by Advanced Micro Devices (AMD), Inc., of Sunnyvale, Calif., as well as any other suitable processor.

Hardware system 1300 may include a variety of system architectures; and various components of hardware system 1300 may be rearranged. For example, cache 1326 may be on-chip with processor 1302. Alternatively, cache 1326 and processor 1302 may be packed together as a "processor module," with processor 1302 being referred to as the "processor core." Furthermore, certain embodiments of the present invention may not require nor include all of the above components. For example, the peripheral devices shown coupled to standard I/O bus 1312 may couple to high performance I/O interface 1310. In addition, in some embodiments only a single bus may exist with the components of hardware system 1300 being coupled to the single bus. Furthermore, hardware system 1300 may include additional components, such as additional processors, storage devices, or memories.

An operating system manages and controls the operation of hardware system 1300, including the input and output of data to and from software applications (not shown). The operating system provides an interface between the software applications being executed on the system and the hardware components of the system. According to one embodiment of the present invention, the operating system is the LINUX operating system. However, the present invention may be used with other suitable operating systems, such as the Windows® 95/9/NT/XP/Server operating system, available from Microsoft Corporation of Redmond, Wash., the Apple Macintosh Operating System, available from Apple Computer Int. of Cupertino, Calif., UNIX operating systems, and the like.

In various embodiments, the Channel Allocation Problem (CAP) is overcome by employing a dynamic channel allocation technique. The dynamic channel allocation technique allows system bandwidth to be allocated to those cells where it is needed. The slow moving nature of patient telemeters allows the global control of time slot and frequency channel allocation, with acceptable complexity of the wireless medical telemetry system and acceptable levels of computational power. This technique may allocate time slots and frequency channels to the Mobile transceivers 104 on a second-by-second basis, i.e., the Mobile transceivers 104 may be monitored, for violation of constraints, on a second-by-second basis.

In other embodiments, a combination of static and dynamic channel allocation techniques may also be employed. In the mixed allocation technique, the mobile transceivers 104 that are not in the process of changing zones may be assigned static channels and the mobile transceivers 104 that are in the process of changing zones may be assigned dynamic channels.

Various embodiments have been described as employing traffic adaptive dynamic channel allocation. In the traffic adaptive technique time slots and frequency channels may be assigned to the Mobile transceivers 104, depending on the traffic conditions prevailing in the Network.

In other embodiments, a re-use adaptive dynamic channel allocation technique may also be employed. The re-use adaptive technique may measure the receive power for all uplink transmitter receiver pairs in the system, allowing frequency re-use to take place whenever it is possible. The Network controller 102 may have to collect power information for all Mobile transceivers 104.

In yet other embodiments an interference adaptive dynamic channel allocation technique may be employed. The interference adaptive technique may measure the environmental interference on all unused channels as well as all used channels, allowing optimization of the signal-to-interference level for all mobile transceivers 104. The network controller 102 may have to collect power measurements on all receive channels at all receivers.

The disclosed methods can be embodied in the form of computer or controller implemented processes and apparatuses for practicing these processes. These methods can also be embodied in the form of computer program code containing instructions embodied in tangible media, such as floppy diskettes, CD-ROMs, hard drives, and the like, wherein, when the computer program code is loaded into and executed by a computer or controller, the computer becomes an apparatus for practicing the method. The methods may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the method. When implemented on a general-purpose microprocessor, the computer program code segments configure the microprocessor to create specific logic circuits.

The technical and scientific terms used herein have the same meaning as is commonly understood by one of skill in the art to which the invention belongs, unless specified otherwise. The terms "first", "second", and the like used herein, do not denote any order or importance, but rather are used to distinguish one element from another. Also, the terms "a" and "an" do not denote a limitation of quantity, but rather denote the presence of at least one of the referenced item.

While the invention has been described in considerable detail with reference to a few exemplary embodiments only, it will be appreciated that it is not intended to limit the invention to these embodiments only, since various modifications, omissions, additions and substitutions may be made to the disclosed embodiments without materially departing from the scope of the invention. In addition, many modifications may be made to adapt to a particular situation or an installation, without departing from the essential scope of the invention. Thus, it must be understood that the above invention has been described by way of illustration and not limitation. Accordingly, it is intended to cover all modifications, omissions, additions, substitutions or the like, which may be included within the scope and the spirit of the invention as defined by the claims.

What is claimed is:

1. A method for reusing radio resources in a medical telemetry network, the method comprising:
   receiving at a server, traffic information for a plurality of mobile transceivers from a plurality of distributed receivers, wherein each of the plurality of mobile transceivers resides in a coverage zone formed by the plurality of distributed receivers;
   identifying time slot assignments and frequency channel assignments of the plurality of mobile transceivers based on the traffic information;
   updating one or more time slot assignments and/or one or more frequency channel assignments based, at least in part, on the traffic information;
   broadcasting updated instances of the time slot assignments and updated instances of frequency channel assignments;
   receiving at the server, error rate of each of the plurality of mobile transceivers;
   comparing the error rate of each of the plurality of mobile transceivers with a maximum permissible error rate; and
   transmitting error correction enable signals to enable error correction on one or more of the plurality of mobile transceivers responsive to the comparison, wherein the error correction comprises:
      transmitting on a first frequency, a first transmission comprising a payload data and a first error detection data associated with the payload data; and transmitting on a second frequency, a second transmission comprising forward error correction data associated with the payload data and a second error detection data associated with the forward error correction data, wherein the forward error correction data comprises parity data generated using an invertible code.

2. The method of claim 1, wherein the updating further comprises taking into account a constraint map, wherein the constraint map comprises channel separation parameters to mitigate co-channel interference, adjacent zone interference and co-site interference.

3. The method of claim 1 wherein the traffic information comprises one or more of number of mobile transceivers in communication with each of a plurality of distributed receivers, a mobile transceiver identifier of the plurality of mobile transceivers, buffer state of the mobile transceiver, and presence of the plurality of mobile transceivers in coverage zones of the plurality of distributed receivers.

4. The method of claim 1 wherein the medical telemetry network operates in the Wireless Medical Telemetry Service (WMTS) spectrum.

5. The method of claim 1 further comprising:
identifying unused time slots in each of a plurality of frequency channels;
identifying for re-assignment, mobile transceivers utilizing time slots immediately following the unused time slots;
updating the time slot assignments and/or the frequency channel assignments of the mobile transceivers identified for re-assignment, to the unused time slots, in order of location of the unused time slots in time and frequency; and
circularly shifting the frequency channel order.

6. The method of claim 1 further comprising:
receiving at the server, the number of time slots required by each of the plurality of mobile transceivers; and
updating the number of time slots assigned to one or more of the plurality of mobile transceivers based on the number of time slots required.

7. The method of claim 1 further comprising:
receiving at the server, transmission power of each of the plurality of mobile transceivers;
comparing the transmission power of each of the plurality of mobile transceivers to a maximum permissible transmission power; and
transmitting a power control signal to adjust the transmission power of one or more of the plurality of mobile transceivers responsive to the comparison.

8. The method of claim 1 further comprising:
updating the number of time slots assigned to the one or more of the plurality of mobile transceivers to allow transmission of error correction data.

9. A system for reusing radio resources in a medical telemetry network, the system comprising:
one or more network interfaces;
one or more processors;
a memory; and
computer program code stored in a computer readable storage medium, wherein the computer program code, when executed, is operative to cause the one or more processors to:
receive at a server, traffic information for a plurality of mobile transceivers from a plurality of distributed receivers, wherein each of the plurality of mobile transceivers resides in a coverage zone formed by the plurality of distributed receivers;
identify time slot assignments and frequency channel assignments of the plurality of mobile transceivers based on the traffic information;
update one or more time slot assignments and/or one or more frequency channel assignments based, at least in part, on the traffic information;
broadcast updated instances of the time slot assignments and updated instances of frequency channel assignments;
receive at the server, error rate of each of the plurality of mobile transceivers;
compare the error rate of each of the plurality of mobile transceivers with a maximum permissible error rate; and
transmit error correction enable signals to enable error correction on one or more of the plurality of mobile transceivers responsive to the comparison, wherein the error correction comprises:
transmitting on a first frequency, a first transmission comprising a payload data and a first error detection data associated with the payload data; and
transmitting on a second frequency, a second transmission comprising forward error correction data associated with the payload data and a second error detection data associated with the forward error correction data, wherein the forward error correction data comprises parity data generated using an invertible code.

10. The system of claim 9 wherein the computer program code is further operative to cause the one or more processors to take into account a constraint map, wherein the constraint map comprises channel separation parameters to mitigate co-channel interference, adjacent zone interference and co-site interference.

11. The system of claim 9 wherein traffic information comprises one or more of number of mobile transceivers in communication with each of a plurality of distributed receivers, a mobile transceiver identifier of the plurality of mobile transceivers, buffer state of the mobile transceiver, and presence of the plurality of mobile transceivers in coverage zones of the plurality of distributed receivers.

12. The system of claim 9 wherein the medical telemetry network operates in the Wireless Medical Telemetry Service (WMTS) spectrum.

13. The system of claim 9 wherein the computer program code is further operative to cause the one or more processors to:
identify unused time slots in each of a plurality of frequency channels;
identify for re-assignment, mobile transceivers utilizing time slots immediately following the unused time slots;
update the time slot assignments and/or the frequency channel assignments of the mobile transceivers identified for re-assignment, to the unused time slots, in order of location of the unused time slots in time and frequency; and
circularly shift the frequency channel order.

14. The system of claim 9 wherein the computer program code is further operative to cause the one or more processors to:
receive at the server, the number of time slots required by each of the plurality of mobile transceivers; and
update the number of time slots assigned to one or more of the plurality of mobile transceivers based on the number of time slots required.

15. The system of claim 9 wherein the computer program code is further operative to cause the one or more processors to:
- receive at the server, transmission power of each of the plurality of mobile transceivers;
- compare the transmission power of each of the plurality of mobile transceivers to a maximum permissible transmission power; and
- transmit a power control signal to adjust the transmission power of one or more of the plurality of mobile transceivers responsive to the comparison.

16. The system of claim 9 wherein the computer program code is further operative to cause the one or more processors to update the number of time slots assigned to the one or more of the plurality of mobile transceivers to allow transmission of error correction data.

17. A computer program product comprising a computer readable medium encoded with computer-executable instructions for reusing radio resources in a medical telemetry network, the computer-executable instructions, when executed, cause one or more processors to:
- receive at a server, traffic information for a plurality of mobile transceivers from a plurality of distributed receivers, wherein each of the plurality of mobile transceivers resides in a coverage zone formed by the plurality of distributed receivers;
- identify time slot assignments and frequency channel assignments of the plurality of mobile transceivers based on the traffic information;
- update one or more time slot assignments and/or one or more frequency channel assignments based, at least in part, on the traffic information;
- broadcast updated instances of the time slot assignments and updated instances of frequency channel assignments;
- further comprising computer-executable instructions operable to cause the one or more processors to:
- receive at the server, error rate of each of the plurality of mobile transceivers;
- compare the error rate of each of the plurality of mobile transceivers with a maximum permissible error rate; and
- transmit error correction enable signals to enable error correction on one or more of the plurality of mobile transceivers responsive to the comparison, wherein the error correction comprises:
  - transmitting on a first frequency, a first transmission comprising a payload data and a first error detection data associated with the payload data; and
  - transmitting on a second frequency, a second transmission comprising forward error correction data associated with the payload data and a second error detection data associated with the forward error correction data, wherein the forward error correction data comprises parity data generated using an invertible code.

18. The computer program product of claim 17 further comprising computer-executable instructions operable to cause the one or more processors to take into account a constraint map, wherein the constraint map comprises channel separation parameters to mitigate co-channel interference, adjacent zone interference and co-site interference.

19. The computer program product of claim 17 wherein traffic information comprises one or more of number of mobile transceivers in communication with each of a plurality of distributed receivers, a mobile transceiver identifier of the plurality of mobile transceivers, buffer state of the mobile transceiver, and presence of the plurality of mobile transceivers in coverage zones of the plurality of distributed receivers.

20. The computer program product of claim 17 wherein the medical telemetry network operates in the Wireless Medical Telemetry Service (WMTS) spectrum.

21. The computer program product of claim 17 further comprising computer-executable instructions operable to cause the one or more processors to:
- identify unused time slots in each of a plurality of frequency channels;
- identify for re-assignment, mobile transceivers utilizing time slots immediately following the unused time slots;
- update the time slot assignments and/or the frequency channel assignments of the mobile transceivers identified for re-assignment, to the unused time slots, in order of location of the unused time slots in time and frequency; and
- circularly shift the frequency channel order.

22. The computer program product of claim 17 further comprising computer-executable instructions operable to:
- receive at the server, the number of time slots required by each of the plurality of mobile transceivers; and
- update the number of time slots assigned to one or more of the plurality of mobile transceivers based on the number of time slots required.

23. The computer program product of claim 17 further comprising computer-executable instructions operable to cause the one or more processors to:
- receive at the server, transmission power of each of the plurality of mobile transceivers;
- compare the transmission power of each of the plurality of mobile transceivers to a maximum permissible transmission power; and
- transmit a power control signal to adjust the transmission power of one or more of the plurality of mobile transceivers responsive to the comparison.

24. The computer program product of claim 17 further comprising computer-executable instructions operable to cause the one or more processors update the number of time slots assigned to the one or more of the plurality of mobile transceivers to allow transmission of error correction data.

* * * * *